US00PP27779P3

(12) United States Plant Patent
Perrault et al.

(10) Patent No.: US PP27,779 P3
(45) Date of Patent: Mar. 14, 2017

(54) HOP PLANT NAMED 'ADHA 871'

(50) Latin Name: *Humulus lupulus*
Varietal Denomination: ADHA 871

(71) Applicants: Jason Perrault, Toppenish, WA (US); Eugene G. Probasco, Yakima, WA (US)

(72) Inventors: Jason Perrault, Toppenish, WA (US); Eugene G. Probasco, Yakima, WA (US)

(73) Assignee: AMERICAN DWARF HOP ASSOCIATION, LLC, Moxee, WA (US)

( * ) Notice: Subject to any disclaimer, the term of this patent is extended or adjusted under 35 U.S.C. 154(b) by 0 days.

(21) Appl. No.: 14/121,499

(22) Filed: Sep. 12, 2014

(65) Prior Publication Data

US 2015/0156939 P1 Jun. 4, 2015

Related U.S. Application Data

(60) Provisional application No. 61/960,260, filed on Sep. 13, 2013.

(51) Int. Cl.
*A01H 5/00* (2006.01)

(52) U.S. Cl.
USPC ..... Plt./236

(58) Field of Classification Search
USPC ..... Plt./236
See application file for complete search history.

(56) References Cited

U.S. PATENT DOCUMENTS

PP23,674 P2 * 6/2013 Jeske et al. ..... Plt./236

* cited by examiner

*Primary Examiner* — Susan McCormick Ewoldt
(74) *Attorney, Agent, or Firm* — Ballew Law

(57) ABSTRACT

A new hop plant named 'ADHA 871' is disclosed. The cones of 'ADHA 871' mature in mid to late September in Moxee, Wash., and yield a crop of 2200 to 2300 pounds per acre. 'ADHA 871' is used for its aromatic quality.

4 Drawing Sheets

Genus and species: *Humulus lupulus*.
Variety denomination: 'ADHA 871'.

STATEMENT REGARDING FEDERALLY SPONSORED RESEARCH OR DEVELOPMENT

None

BACKGROUND OF THE INVENTION

'ADHA 871' is a product of a controlled breeding program carried out by the inventor in the Yakima Valley of Washington State. 'ADHA 871' was one of several seedlings resulting from cross number 08-071 made in 2008 with female parent 'ADHA 538' (not patented) which was open pollinated with male hops plants. A single plant of 'ADHA 871' was selected in 2009.

In 2011 that single plant was expanded by asexual propagation using softwood cuttings into a large scale test plot in Moxee, Wash. for further observation and evaluation. Subsequent evaluations of that test plot show that 'ADHA 871' has been observed through several generations to retain its distinctive characteristics after asexual propagation, and has remained true to type.

BRIEF DESCRIPTION OF THE PHOTOGRAPHS

FIG. 3 illustrates the bine of a mature 'ADHA 871' hop plant; and.

Figure 1:
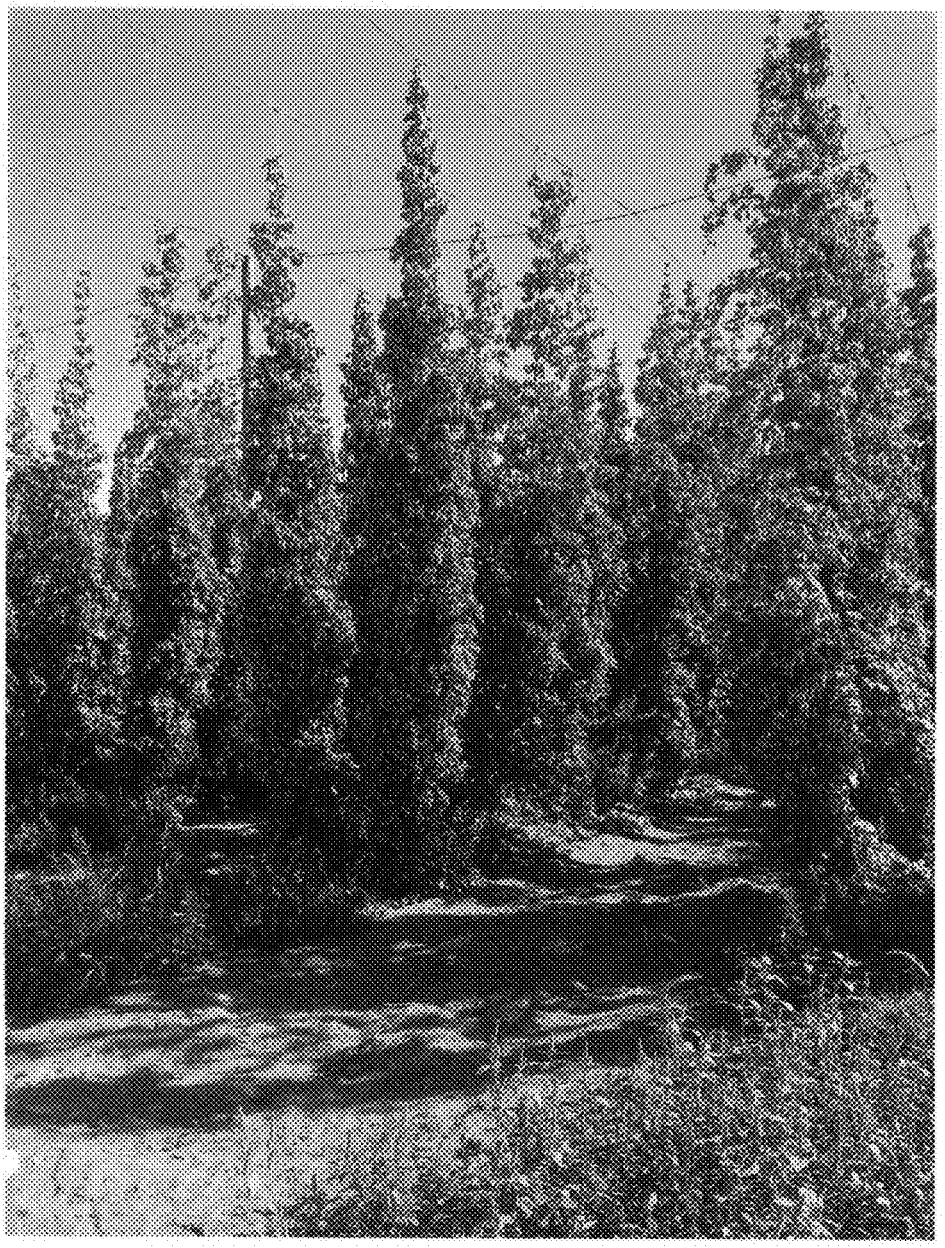
FIG. 1 illustrates a mature 'ADHA 871' hop plant grown on a trellis.
Figure 2:
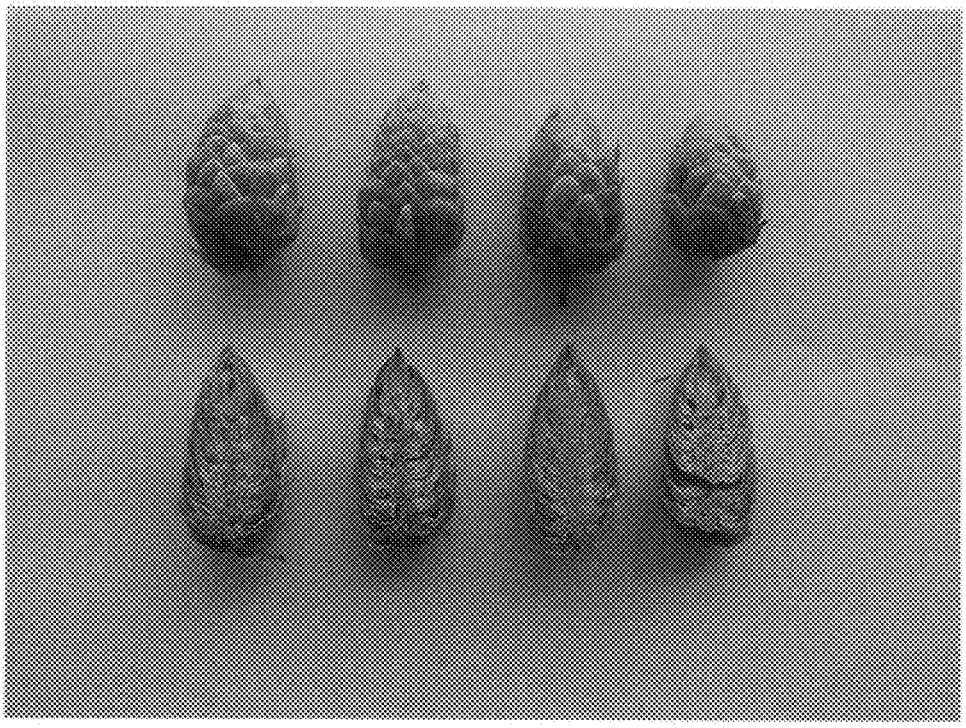
FIG. 2 illustrates whole cones and cross sections of cones of the 'ADHA 871' hop plant.
Figure 3:
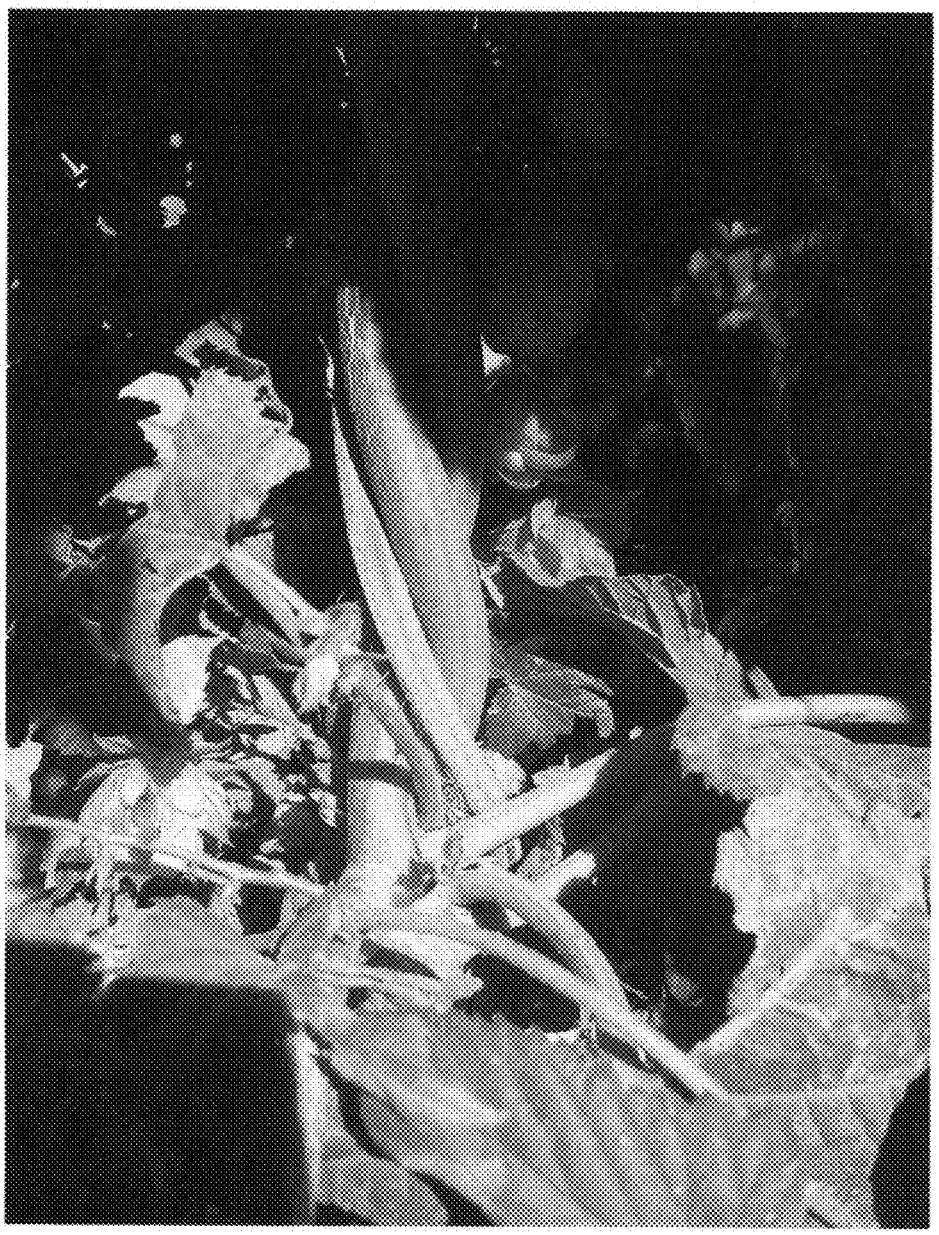
Figure 4:
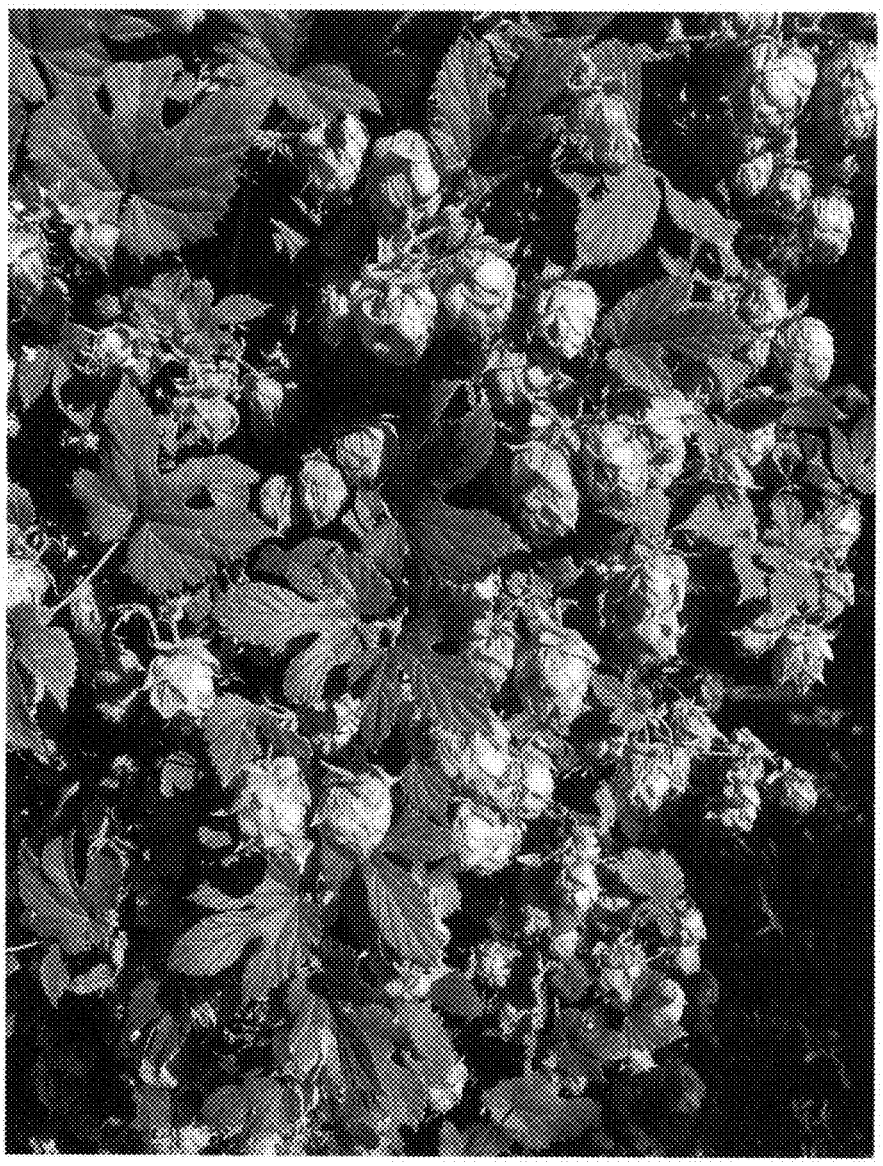
FIG. 4 illustrates the cones and leaves of a mature 'ADHA 871' hop plant.

The colors of these illustrations may vary with lighting conditions and, therefore, color characteristics of this new variety should be determined with reference to the observations described herein, rather than from these illustrations alone.

DETAILED BOTANICAL DESCRIPTION

The following description is based on observations made during the 2013 growing season at Moxee, Wash.

'ADHA 871' is distinguishable from its parent plants ('ADHA 538t' mother (unpatented) and unknown male parent. 'ADHA 871' is distinguishable from all male plants because 'ADHA 871' is a female plant with flowers that develop into mature hop cones without producing pollen, while flowers of all male hop plants will always produce pollen without developing into mature hop cones.

Table 1. sets forth some of the distinguishing characteristics of 'ADHA 871' as compared to its female parent 'ADHA 538', and to the hop variety 'Summit':

TABLE 1

| Characteristic | 'ADHA 538' | 'ADHA 871' | 'Summit' |
|---|---|---|---|
| Alpha Acid (α-Acids, % db) | 16-17 | 13-16 | 18-19 |
| Beta Acids (β-Fraction, % db) | 6.0-6.5 | 3.5-4.25 | 3.3-4.3 |

TABLE 1-continued

| Characteristic | 'ADHA 538' | 'ADHA 871' | 'Summit' |
|---|---|---|---|
| Total Oil (ml/100 g) | 2.8 | 2.1-2.7 | 1.5 |
| Myrcene (% of Total Oil) | 62.75 | 46-55 | 48.5 |

It should be understood that the characteristics described will vary somewhat depending upon cultural practices and climatic conditions, and can vary with location and season. Quantified measurements are expressed as an average of measurements taken from a number of individual plants of the new variety. The measurements of any individual plant or any group of plants, of the new variety may vary from the stated average. The color chart used was The Royal Horticultural Society Colour Chart, Copyright 2001, and all color observations were made outdoors in full sunlight.

Ploidy: Diploid.

Use: Brewing beer.

Harvest date: September 15 to 25 during the 2009-2012 growing seasons, Moxee, Wash.

Time of flowering: Considered to be late compared to other common hop varieties hop varieties grown in Central Washington.

Crop yield: 2200 to 2300 pounds per acre.

Disease susceptibility: Tolerant of both downy mildew and powdery mildew.

Pest susceptibility: Average susceptibility to pests, including hop aphids and two spotted spider mites.

Plant shape: Columnar when grown on a typical hop trellis.

Bine:

*Color*.—Green Group 144B.

*Stripe*.—Present, Red Purple 59A.

*Bine diameter*.—10 mm at base; 10 mm at 9eet; and no measurement taken at terminal end.

*Stipule direction*.—Upward forked.

*Stipule color*.—Green Group 145A.

Leaf:

*Leaf arrangement*.—Opposite.

*Mature leaf shape*.—Palamtely lobed.

*Color of mature leaf upper surface*.—Green Group 139A.

*Color of mature leaf lower surface*.—Green Group 137B.

*Average length of mature leaf*.—12.

*Average width of mature leaf*.—18.

*Number of lobes*.—3-7.

*Margin*.—Serrate.

*Serrations per inch*.—5-7.

*Vein color*.—Green Group 145A.

Petiole:

*Average petiole length* (*mature*).—8.0 cm.

*Petiole color at base*.—Yellow Green 144A w/Red Purple.

Cone:

*Cone shape*.—Ovoid.

*Lupulin gland color*.—Ranging between Golden Yellow 2A to Yellow Green 150A (not distinctive of this variety).

*Lupulin gland shape*.—Pedunculated oblong polyps.

*Lupulin gland number*.—Medium number per cone.

Bracts:

*Bract tip shape*.—Cuspidate alternating with rounded.

*Bract tip position*.—Loosely appressed.

*Bract tip color*.—Yellow Green Group 144A.

*Bract base color*.—Yellow Green Group 145D.

Bracteoles:

*Bracteole color*.—Yellow Green Group 144A.

*Bracteole shape*.—Cuspidate Orbicular.

Analytical characteristics:

*Alpha acid*.—13-16%.

*Beta acid*.—3.5-4.25%.

*Cohumulone*.—27-30%.

*Humulene*.—12-15% of total oils.

*Caryophyllene*.—11-13% of total oils.

*Myrcene*.—46-55% of total oils.

*Farnesene*.—<1% of total oil.

*Total oil*.—2.1-2.7 ml/100 g.

*Hop storage index* (*HSI*).—The cones of the present variety experience a 25.2% transformation of alpha acids after about 6 months of storage at 22° C.

What is claimed is:

1. A new and distinct hop plant as shown and described herein.

* * * * *